(12) United States Patent
Hlinka et al.

(10) Patent No.: US 9,944,892 B2
(45) Date of Patent: Apr. 17, 2018

(54) STRUCTURE FOR CULTURING CELLS

(71) Applicant: DDNT Consultants Australia Pty Ltd, Sydney (AU)

(72) Inventors: Daniel Hlinka, Sydney (AU); Ljubomir Lazarovski, Sydney (AU); Dalibor Frtunik, Sydney (AU); Tomislav Frtunik, Sydney (AU)

(73) Assignee: DDNT CONSULTANTS AUSTRALIA PTY LTD, Sydney (AU)

( * ) Notice: Subject to any disclaimer, the term of this patent is extended or adjusted under 35 U.S.C. 154(b) by 210 days.

(21) Appl. No.: 14/770,011

(22) PCT Filed: Feb. 25, 2014

(86) PCT No.: PCT/AU2014/000172
§ 371 (c)(1),
(2) Date: Aug. 24, 2015

(87) PCT Pub. No.: WO2014/131079
PCT Pub. Date: Sep. 4, 2014

(65) Prior Publication Data
US 2016/0002583 A1    Jan. 7, 2016

(30) Foreign Application Priority Data

Feb. 26, 2013    (AU) .................... 2013900676

(51) Int. Cl.
| | | |
|---|---|---|
| C12M 3/00 | (2006.01) | |
| C12M 1/22 | (2006.01) | |
| C12M 1/32 | (2006.01) | |
| C12M 1/00 | (2006.01) | |
| B01L 3/00 | (2006.01) | |
| C12M 1/12 | (2006.01) | |

(52) U.S. Cl.
CPC ........... *C12M 21/06* (2013.01); *B01L 3/5085* (2013.01); *C12M 23/10* (2013.01); *C12M 23/12* (2013.01);
(Continued)

(58) Field of Classification Search
CPC ...... C12M 21/06; C12M 23/10; C12M 23/12; C12M 23/16; B01L 3/502;
(Continued)

(56) References Cited

U.S. PATENT DOCUMENTS

| 4,945,061 A | 7/1990 | Iskander |
| 5,856,176 A * | 1/1999 | Mathus ............... C12M 23/52 220/755 |

(Continued)

FOREIGN PATENT DOCUMENTS

| CN | 102876563 A | 1/2013 | |
| JP | 2001112464 A * | 4/2001 | ............ C12M 23/10 |

(Continued)

OTHER PUBLICATIONS

Extended European Search Report dated Oct. 14, 2016 in corresponding application No. 14757747.2.
(Continued)

*Primary Examiner* — William H. Beisner
(74) *Attorney, Agent, or Firm* — Knobbe, Martens, Olson & Bear, LLP

(57) ABSTRACT

The present invention relates to a structure and a container for culturing cells. In one arrangement, the structure (200) comprises a partially enclosed cavity (204) and a plurality of compartments (201) adapted for fluid communication with the partially enclosed cavity (204). Each compartment (201) is configured to hold one or more cell within its compartment (201) at a location dependent on a dimension of the cell. This arrangement may facilitate visual identification or indication of the size of the cell by observing its location within its compartment (201). The structure (200) may be included or formed integrally with a container (100) such as a Petri dish.

24 Claims, 14 Drawing Sheets

(52) U.S. Cl.
CPC ............ *C12M 23/20* (2013.01); *C12M 23/22* (2013.01); *C12M 23/34* (2013.01); *C12M 23/38* (2013.01); *C12M 23/48* (2013.01); *C12M 25/00* (2013.01); *B01L 2200/0668* (2013.01); *B01L 2300/0803* (2013.01); *B01L 2300/0851* (2013.01); *B01L 2300/0864* (2013.01)

(58) Field of Classification Search
CPC ..... B01L 2200/0668; B01L 2300/0803; B01L 2300/0851; B01L 2300/0864
See application file for complete search history.

(56) References Cited

U.S. PATENT DOCUMENTS

| | | | |
|---|---|---|---|
| 6,410,310 | B1 | 6/2002 | Flegal et al. |
| 7,186,548 | B2 | 3/2007 | Li |
| 7,820,433 | B2 | 10/2010 | Larsen |
| 7,915,034 | B2 | 3/2011 | Cecchi et al. |
| 2010/0075411 | A1 | 3/2010 | Cecchi |
| 2010/0174133 | A1 | 7/2010 | Cohen et al. |
| 2012/0003682 | A1 | 1/2012 | Thomas et al. |

FOREIGN PATENT DOCUMENTS

| | | | | |
|---|---|---|---|---|
| WO | 2011/055560 | A | 5/2011 | |
| WO | 2011/118211 | A | 9/2011 | |
| WO | 2012/094956 | A | 7/2012 | |
| WO | WO 2012094956 | A1 * | 7/2012 | ............ C12M 21/06 |

OTHER PUBLICATIONS

Notice of Rejection in Japanese Application No. 2015-558309 dated Jan. 23, 2018 in 8 pages (English translation included).

\* cited by examiner

STRUCTURE FOR CULTURING CELLS

CROSS-REFERENCE TO RELATED APPLICATIONS

This application is the U.S. National Phase under 35. U.S.C. § 371 of International Application PCT/AU2014/000172, filed Feb. 25, 2014, which claims priority to Australian Patent Application No. 2013900676, filed Feb. 26, 2013. The disclosures of the above- described applications are hereby incorporated by reference in their entirety.

FIELD OF THE INVENTION

The present invention relates to a structure and a container for culturing cells. In particular, the invention relates to a structure and a container with multiple compartments each for culturing one or more cells.

BACKGROUND OF THE INVENTION

Glass or plastic vessels modelled on the original Petri dish remain a standard for culturing cells. Such vessels however lack effectiveness for specific applications such as in vitro fertilisation (IVF). For example, in IVF, a Petri dish may not be most suited for culturing multiple eggs at once. Furthermore, it is difficult to locate a fertilised egg or to monitor the growth or progress of an egg on a Petri dish.

Improvements are known that place a number of small indented wells on a single dish. This allows multiple eggs to be fertilised in close proximity, which has been related to improved embryo viability. Indented wells may also make it easier to locate eggs and monitor them with various automated systems. Other improvements are known that employ a spoked-wheel design to keep eggs in close proximity for identification.

The present invention aims to overcome problems with the prior art and/or provide an alternative for cell culture.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

According to a first aspect of the invention there is provided a structure for use with a container for culturing multiple cells, the structure comprising:
a partially enclosed cavity; and
a plurality of compartments each having a proximal end adjacent the partially enclosed cavity and a distal end remote from the partially enclosed cavity, each compartment being adapted for fluid communication with the partially enclosed cavity.
wherein each compartment is configured to hold a cell at a location between the proximal end and the distal end, and at least a portion of each compartment is shaped to increase in width towards the proximal end.

Embodiments of the invention may therefore facilitate visual identification or indication of the size of the cell by observing its location within its compartment.

The plurality of compartments may be each shaped to direct the cell towards the distal end of the respective compartment. The plurality of compartments may each include a sloped base for directing the cell towards the distal end of the respective compartment. The sloped base may be downwardly sloped towards the distal end. Alternatively or additionally the sloped base includes one or more grooves.

At least one of the plurality of compartments may be adapted for direct fluid communication with another one of the plurality of compartments. The structure may include one or more inter-compartment channels for facilitating the direct fluid communication between adjacent compartments.

The structure may include one or more access channels or one or more openings for facilitating fluid communication between the partially enclosed cavity and respective one or more compartments.

The structure may include the one or more access channels or the one or more openings for facilitating access by a microtool.

The structure may further comprise:
an inner barrier for defining the partially enclosed cavity; and
an outer barrier for defining the plurality of compartments between the inner barrier and the outer barrier.

The inner barrier may include closely spaced posts. The closely spaced posts may include one or more of circular posts, triangular posts and polygonal posts. The closely spaced posts may define the one or more access channels or the one or more openings.

The structure may further comprise a wall coupled to the outer barrier for containing a culture medium.

The cavity may include a central cavity surrounded by the plurality of compartments. The plurality of compartments may be equidistant or substantially equidistant from the central cavity.

Preferably each of the plurality of compartments is labelled. More preferably the labelling includes any one or more of etching, engraving, embossing and molding.

Each of the plurality of compartments may be configured to hold more than one cell.

The cell may include any one or more of a sperm cell, an egg cell, an oocyte, a zygote, a blastoma, or any other cell. The cell may for example be a human, bovine, ovine, porcine, or murine cell.

According to a second aspect of the invention there is provided a structure for use with a container for culturing multiple cells, the structure comprising:
a partially enclosed cavity; and
a plurality of compartments each being:
adapted for fluid communication with the partially enclosed cavity; and
configured to hold a cell within its compartment at a location dependent on a dimension of the cell, wherein at least one of the plurality of compartments is adapted for direct fluid communication with another one of the plurality of compartments.

According to a third aspect of the invention there is provided a container including or formed integrally with a structure as defined the first aspect or the second aspect.

The structure is one of a plurality of structures included or formed integrally with the container.

The container may include one or more processing wells for intermediate cell culture procedures.

The container may include one or more supports for elevating the container to permit airflow underneath the container.

The container may include protrusions arranged around its lid to facilitate orientation or stacking. The protrusions may be distributed evenly around the lid. Alternatively the protrusions may be distributed unevenly around the lid.

The container may include indentations arranged around its base to facilitate orientation, stacking or rotation. The indentations may be distributed evenly around the base. Alternatively the indentations may be distributed unevenly around the base.

A combination of indentations and protrusions arranged symmetrically, or asymmetrically to facilitate orientation.

The container may have features facilitating identification of the dish, such as a space for a label to be affixed or a name drawn with a marker without affecting the microscope transparency of the central features.

The container may have a lid used to prevent contamination of the contents and reduce the evaporation of cell culture medium employed in the dish features.

The lid may contain one or more central downward protrusion covering the edges of structures inside the petri dish to further reduce evaporation and potential contamination.

The lid may contain indentations or protrusions on its upper surface facilitating stacking of dishes with a lid.

The lid may contain features compatible with the container's features for identification of the dish, such as space for a label that overlaps that of the dish, or a clear space revealing an identifying label beneath while enabling interchange of lids between dishes.

The container may contain a rim facilitating lifting of the dish by a human hand or automated gripper without contacting the lid, which may slide off and cause a dish to fall.

At least part of the container may be coated with a coating for one or more of the following: reducing formation of air bubbles caused by flow of the cell culture medium in the container, enhancing adhesion of the cells to a container surface, improving transparency of the container, and improving viability of the cells cultured in the container. The coating may include a hydrophilic or oleophobic substance.

The container may be a sample dish. The sample dish may be a Petri dish.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

The present invention generally relates to a structure and a container for culturing cells. In particular, the invention relates to a structure with multiple compartments each for culturing one or more cells. As discussed further below, the arrangements may facilitate visual identification or indication of the size of the cell by observing its location within the corresponding compartment.

The described structure may be located in a container (such as a glass or plastic sample dish including a Petri dish) for culturing multiple cells. In broad terms, the structure comprises a partially enclosed cavity and a plurality of compartments each including a proximal end adjacent the cavity and a distal end remote from the cavity and each compartment being adapted for fluid communication with the partially enclosed cavity, wherein each compartment is configured to hold a cell at a location between the proximal end and the distal end and at least a portion of each compartment is shaped to increase in width towards the proximal end.

Figure 1A:
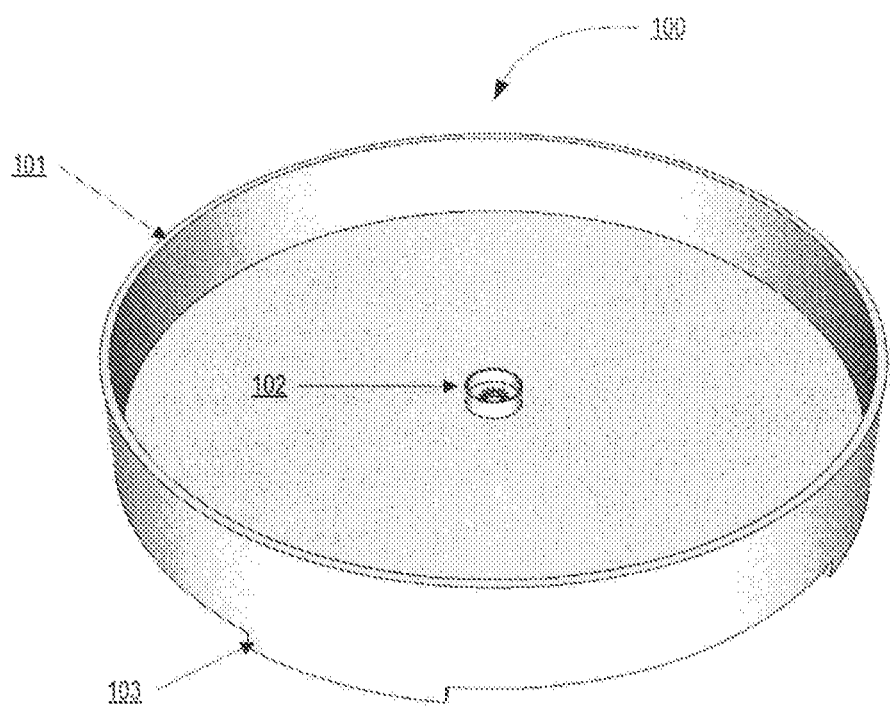
FIGS. 1A and 1B illustrate a perspective view and a top view of an embodiment of a container for culturing cells.
Figure 1B:
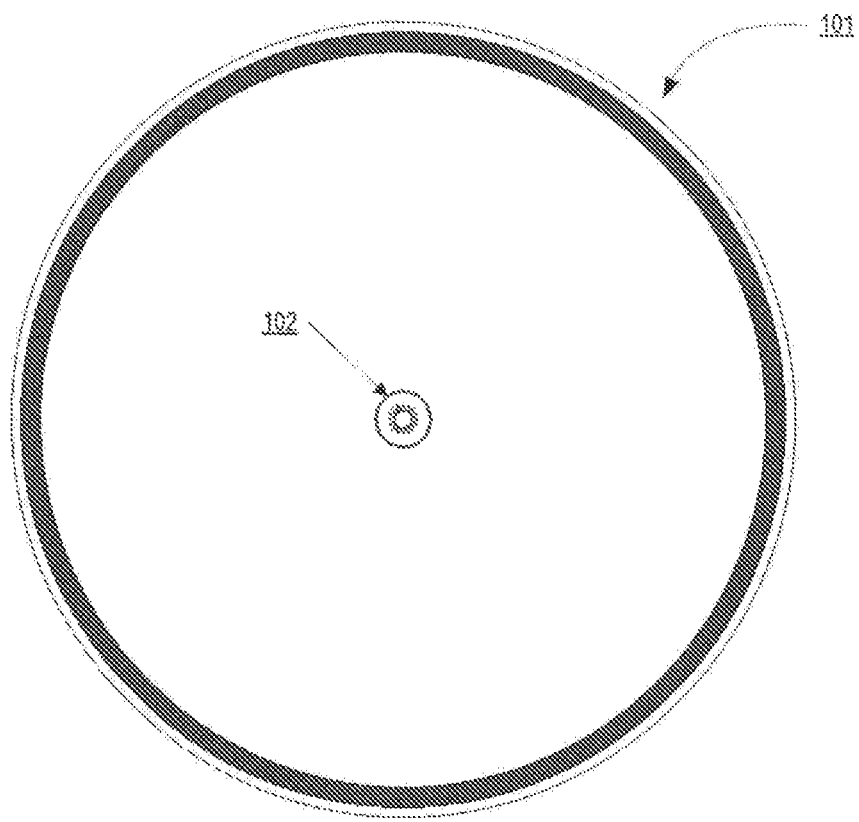

Also described herein is a container (such as a glass or plastic sample dish including a Petri dish) including or formed integrally with the structure. FIGS. 1A and 1B show a perspective view and a top view, respectively, of an embodiment of a container. The container is a sample dish 100 with dish wall 101 and structure 102 formed integrally with the sample dish 100. In some embodiments, the structure may be separable from the sample dish. The sample dish may include a lid with notched edges that are suitable for stacking to reduce lateral movement between stacked sample dishes, as described in prior art. Examples of the structure are illustrated in FIGS. 2A to 4B and are described further below.

The described container or the structure may be wholly or partially transparent, semi-transparent or opaque. The accompanying figures serve to illustrate structural aspects, and are not intended to reflect the transparency or opaqueness of the described container or structure.

Referring to FIGS. 1A and 1B, structure 102 may be located at or near the centre of the sample dish 100. Although not shown, a number of structures may be located in the sample dish. The general shape of the container may be similar to that of a standard Petri dish, having a flat base and a cylindrical wall surrounding the base. In this embodiment, sample dish 100 may include one or more supports on the outer bottom surface for elevating sample dish 100. For example, container 100 includes stilts 103 which permit airflow underneath sample dish 100, thereby preventing condensation. In other embodiments, the container may take the shape of a standard Petri dish, having a substantially flat bottom part that rests on a support surface.

Figure 2A:
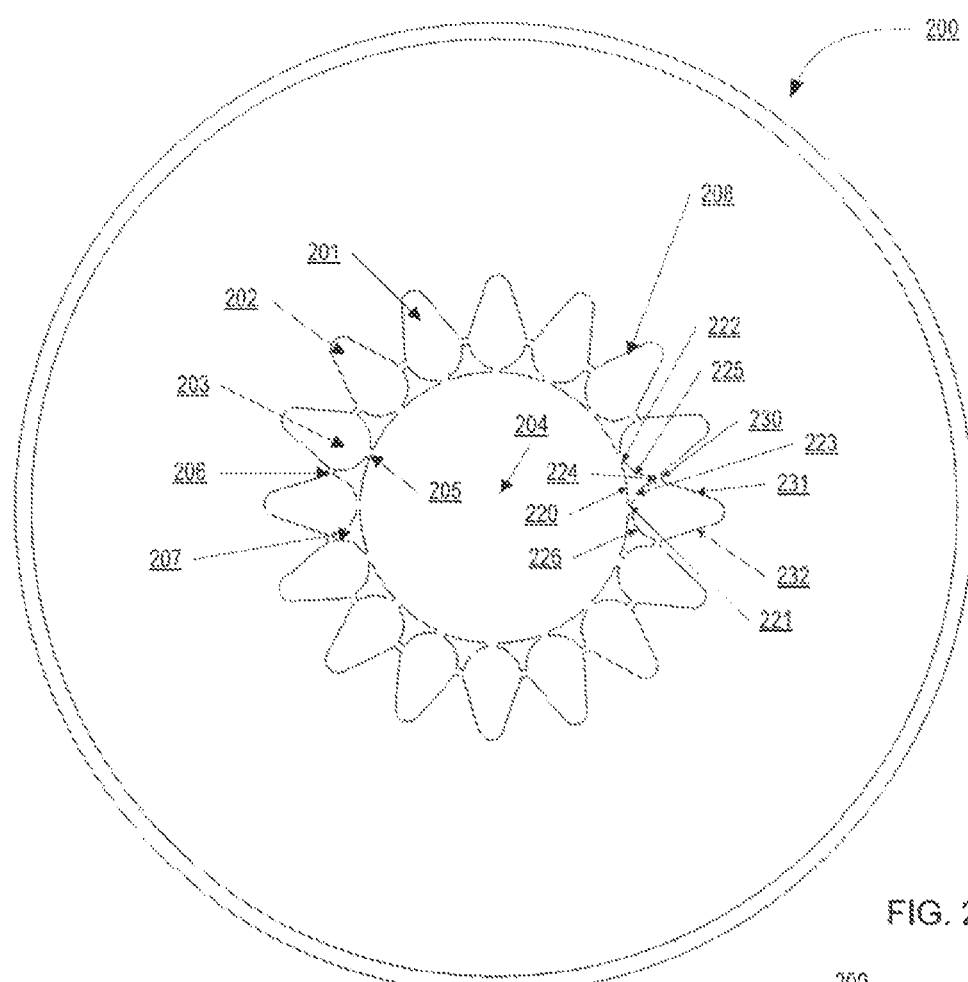
FIGS. 2A and 2B illustrate a top view and a perspective view of a first embodiment of a structure for use in the container of FIGS. 1A and 1B.
Figure 2B:
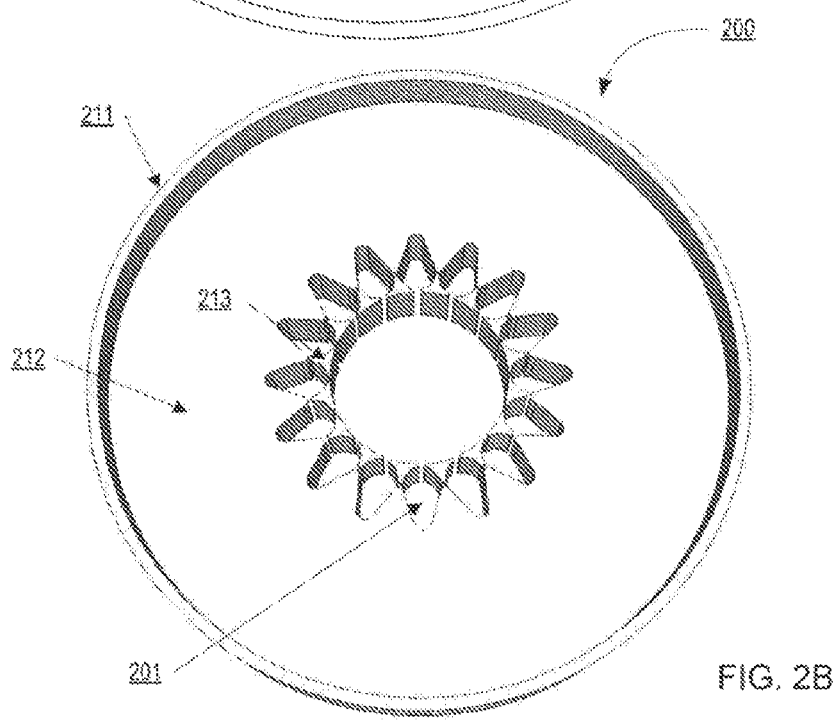

FIGS. 2A and 2B illustrate an embodiment of a structure 200, which is an enlarged view of structure 102 illustrated in FIGS. 1A and 1B. FIG. 2A is a top view of structure 200 while FIG. 2B is a perspective view of structure 200. Structure 200 may include a partially enclosed cavity, such as central cavity 204, and a plurality of compartments 201 surrounding central cavity 204. The plurality of compartments 201 may be equidistant or substantially equidistant from the central cavity 204. Each compartment may include a wider proximal end 203 (adjacent central cavity 204) and a narrower distal end 202 (remote from central cavity 204). One or more cells may be held and cultured in each of the compartments at a location between proximal end 203 and distal end 202. As illustrated in FIGS. 2A and 2B, each compartment is shaped to increase in width towards its proximal end. The rate of increase in width may be constant, resulting in straight compartment wall(s) 208. Alternatively the rate of increase in width may vary, resulting in curved compartment wall(s) (not shown). In general, at least a portion of each compartment is shaped to increase in width towards its proximal end. It is envisaged that the dimension of distal end 202 is such that it is suitable for holding a small or growing cell (such as an oocyte or zygote) to be cultured, while the dimension of proximal end 203 is such that it is able to accommodate a partially grown cell (such as a 4-cell blastoma) that is ready for subsequent harvest, transfer or use. The dimensions of the compartments may be adapted to better fit cells of specific species, such as human, bovine, ovine, porcine or murine cells.

In some embodiments, the length of the compartments may vary across different compartments and/or across different structures. Using compartments of a different length may be useful in certain situations. For example, a longer compartment implies a more gradual change in compartment width towards the central cavity. For the same amount of growth, a cell being cultured in a longer compartment may therefore move towards the central cavity by a greater distance. It then follows that the longer compartment may provide a clearer indication.

In some embodiments, the compartments are each shaped to direct the cell towards the distal end of the respective compartment. For example, the plurality of compartments may each include a sloped base, for example, towards the distal end 202.

Due to gravity, the cell may be directed towards the distal end 202 of the respective compartment. In some embodiments, the sloped base may include one or more grooves. The grooves may run substantially between the proximal end and the distal end. The orientation of the grooves ensures, for example, that the cell rests at or near the central axis of the compartment, or near the outside of the compartment (depending on the type and number of cells being cultured). The grooves are also thought to facilitate cell growth in certain circumstances.

Each compartment may be adapted for fluid communication with central cavity 204. For example, in the embodiment illustrated in FIGS. 2A and 2B, structure 200 includes one or more access channels 205 for facilitating fluid communication between central cavity 204 and respective compartments. In some embodiments, the access channels may be adapted for facilitating access by a microtool. Microtool access through the access channels may be useful in circumstances such as when fertilising an oocyte with a microtool. Alternatively or additionally, a microtool may access a compartment from above the compartment structure in circumstances such as when removing a blastoma for implantation. As another example, the structure may include one or more openings for facilitating fluid communication between central 204 cavity and respective one or more compartments. The widest part of each compartment may be sufficiently far from the widest part of adjacent compartments so that when a tool is used to remove a large, mature cell, mature cells in adjacent apartments are unlikely to be also drawn up with it. The same is true of the narrowest part.

An illustrative example of a use of structure 200 is provided as follows. A cell such as an oocyte may be placed within compartment 201. Due to its relatively small size, the oocyte may be held or pinned relatively close to distal end 202. This may be achieved by extending a microtool via access channel 205 to push the oocyte towards distal end 202 where the cell may rest. This manipulation may be useful during in vitro fertilisation (IVF). As the cell grows in size, the increase in the width of the compartment towards proximal end 203 means that the growing cell gradually moves towards proximal end 203. In particular, either or both of the centre of the cell and the boundary of the cell may move towards proximal end 203. For example, human oocytes are ~160 μm in diameter, while a blastoma ready for use in an IVF procedure may be as large as 350-360 μm. Other species may have different oocyte and blastoma sizes. For example, mouse oocytes and blastomas may be approximately 40 μm and 80 μm respectively. In general, the larger the cell becomes, the closer the cell moves towards proximal end 203. Accordingly, structure 200 facilitates visual identification or indication of the size, and hence the growth, of the cell by observing its location, such as its centre or boundary, within the compartment.

In some embodiments, one or more compartments may increase in width towards their respective distal end. That is, the distal end may be wider than the proximal end. In these embodiments, the compartments may guide or indicate cell growth from the proximal end to the distal end. Furthermore, one or more access channels may be provided at or near the distal ends of the compartments or the perimeter of the structure to provide access by a microtool.

As the dimensions of the compartments may be varied based on the species that is being cultured, the number of compartments may also be varied—either to provide an optimal distribution of compartments (e.g. more compartments can be fit into a structure for culturing mouse cells compared with one for culturing human cells) or to optimize the distance between adjacent compartments (e.g. structures with fewer compartments may not be optimal as this would render the central cavity too small or the inter-compartment channels too long). FIGS. 2A and 2B illustrate a 16-compartment structure but a structure may have 12 compartments, 24 compartments, or any other number of compartments as required.

In some embodiments, at least one of the plurality of compartments may be adapted for direct fluid communication with another one of the plurality of compartments. For example, in the embodiment illustrated in FIGS. 2A and 2B, structure 200 includes inter-compartment channels 206 for facilitating direct fluid communication between adjacent compartments. This may be beneficial for growth of some types of cells. For example, it has been reported that culturing fertilised eggs in close proximity may be related to improved embryo viability. Accordingly, while multiple cells may each be held or confined to their own compartment, inter-compartment channels may allow fluid communication between adjacent compartments to increase biochemical reaction between cells held or confined in separate compartments.

In FIGS. 2A and 2B, structure 200 includes an inner barrier 213 defining central cavity 204 and an outer barrier 212 for defining the plurality of compartments 201 between inner barrier 213 and outer barrier 212. As illustrated in FIG. 2B, the inner and outer barriers may each be radially symmetrical.

The inner barrier may be formed by closely spaced posts 207 defining the one or more access channels 205, or the one or more openings as described above. In the depicted arrangement, each post 207 has six surfaces. A first surface 220 is curved and defines a portion of the circumference of central cavity 204. Collectively the surfaces 220 of all posts 207 define the central cavity 204. A second surface 221 and a third surface 222 are flat surfaces and are each facing a corresponding surface of an adjacent post. Each pair of corresponding surfaces defines an access channel 205 or an opening to provide fluid communication with central cavity 204. A fourth surface 223 is a curved surface and forms a portion of the boundary of a compartment, whereas a fifth surface 225 is also a curved surfaces and forms a portion of the boundary of an adjacent compartment. The fourth surface 223 and a corresponding curved surface 226 of an adjacent post, together with flat surfaces 231 and 232 of outer barrier 212, define the boundary of a compartment. A sixth surface 224 of post 207 is a flat surface and is facing a corresponding surface 230 of the outer barrier 212. Together surface 224 and corresponding surface 230 define an inter-compartment channel 206. In FIG. 2A, surfaces 231 and 232 of outer barrier 212 are depicted as flat so that the rate of increase of width of the compartment towards the proximal end is constant. In other embodiments, these two surfaces of the outer barrier may be curved so that the rate of increase of width of the compartment towards the proximal end varies.

Figure 3A:
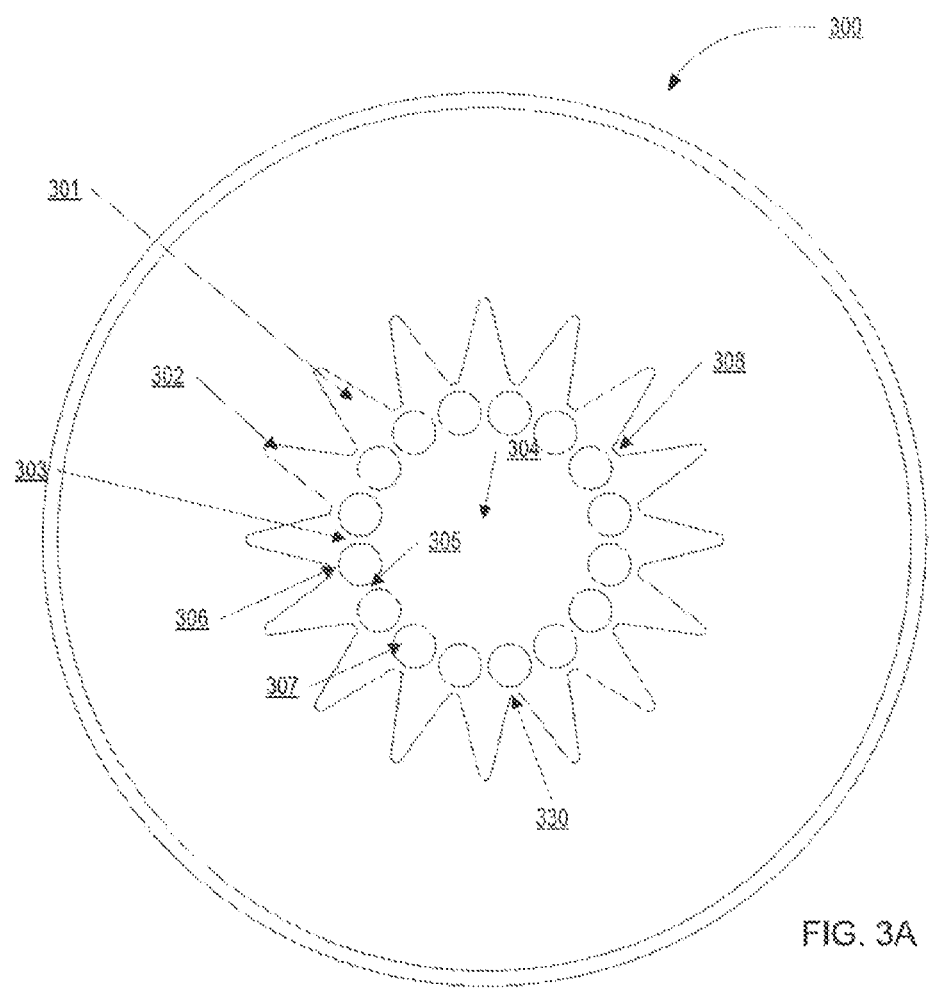
FIGS. 3A and 3B illustrate a top view and a perspective view of a second embodiment of the structure for use in the container of FIGS. 1A and 1B.
Figure 3B:
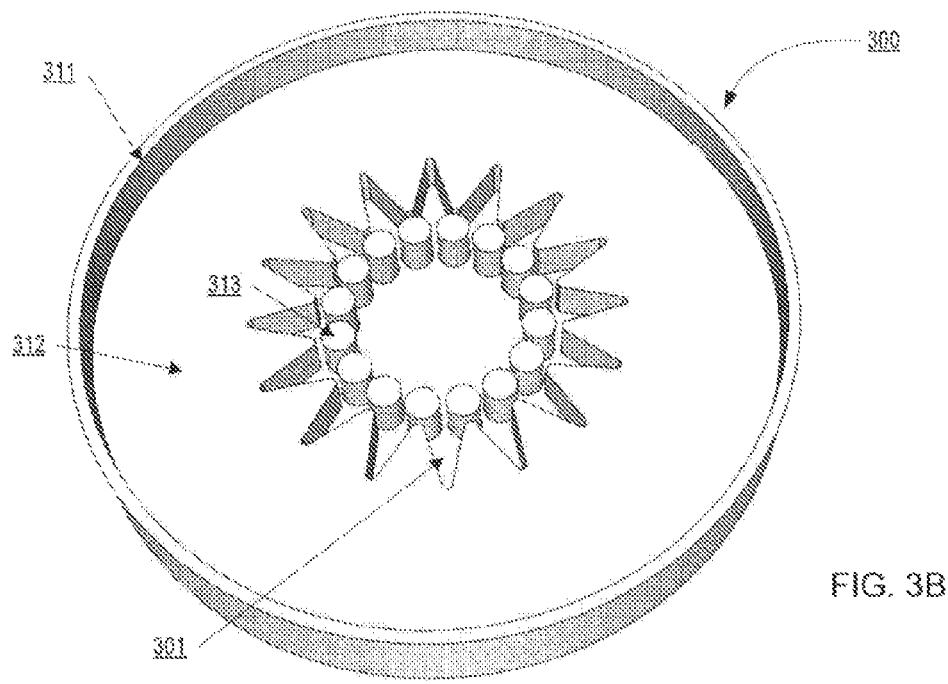

In the embodiment shown in FIGS. 2A and 2B, the closely spaced posts 207 are polygonal posts. In other embodiments, the closely spaced posts may be of a different shape. For example, as illustrated in FIGS. 3A and 3B, structure 300 may include closely spaced posts which are cylindrical posts 307. Features of structure 300 corresponding to those in structure 200 are labelled using the same reference numerals except that they are prefixed by the number "3" instead of the number "2". A pair of adjacent circular posts may define an access channel 305 or an opening to provide fluid communication between compartment 301 and central cavity 304. Inter-compartment channel 306 may be defined by a gap between circular post 307 and a surface 330 of the outer barrier 312.

Figure 4A:
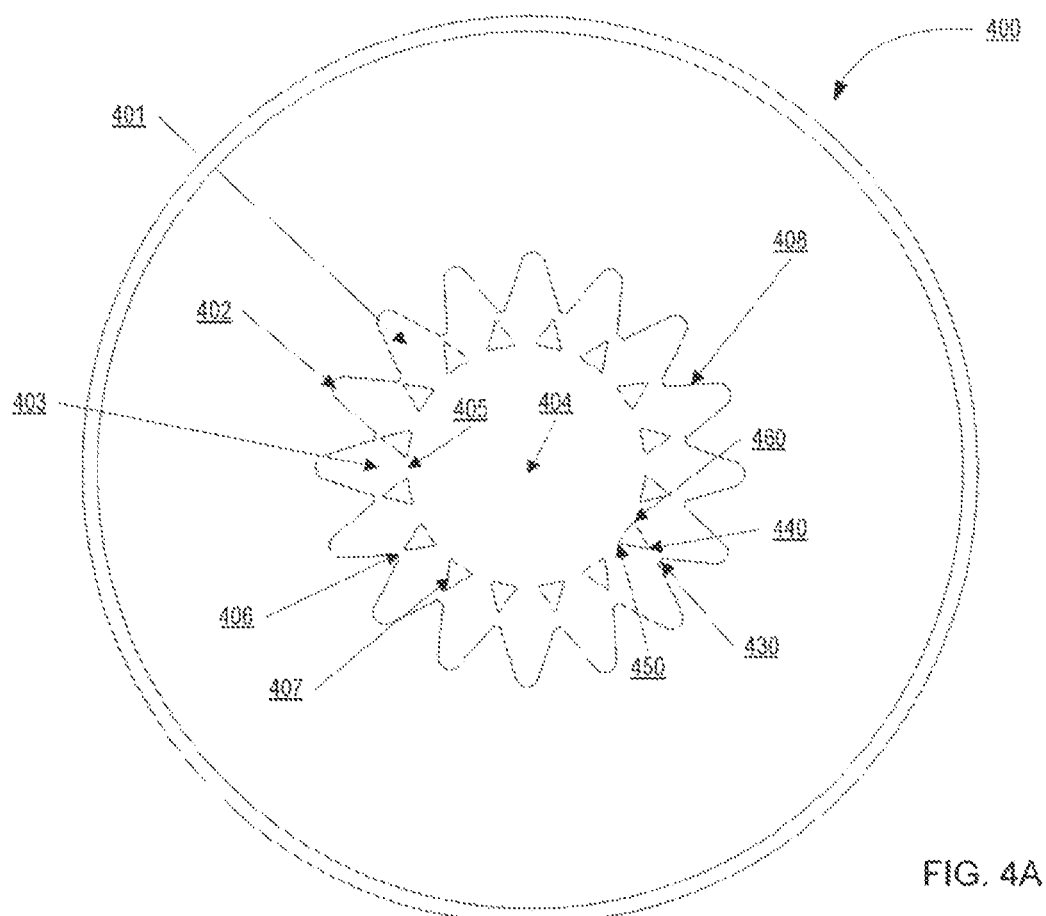
FIGS. 4A and 4B illustrate a top view and a perspective view of a third embodiment of the structure for use in the container of FIGS. 1A and 1B.
Figure 4B:
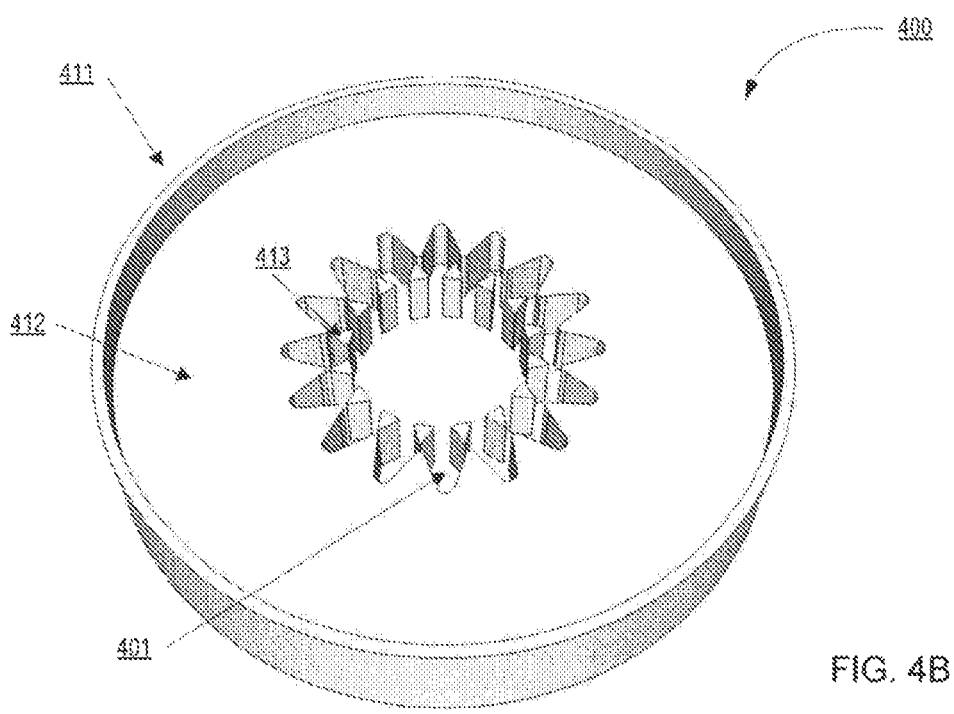

As another example, as illustrated in FIGS. 4A and 4B, structure 400 may include closely spaced posts which are triangular posts 407. Features of structure 400 corresponding to those in structure 200 are labelled using the same reference numerals except that they are prefixed by the number "4" instead of the number "2". A pair of adjacent triangular posts may define an opening 405 between two apexes 450 and 460 to provide fluid communication between compartment 401 and central cavity 404. Inter-compartment channel 406 may be defined by a gap between an apex 440 of triangular post 307 and a surface 430 of the outer barrier 412.

Structure 200 may include a wall 211 coupled to outer barrier 212 for containing a culture medium. Wall 211 may extend vertically from the top surface of outer barrier 212. The height of wall 211 may in part determine the volume of culture medium that is able to be kept within wall 211. Each of the plurality of compartments 201 may be labelled, for example, on the top surface of outer barrier 212 for identification purposes. The labelling may include any one or more of etching, engraving, embossing and molding.

Figure 5A:
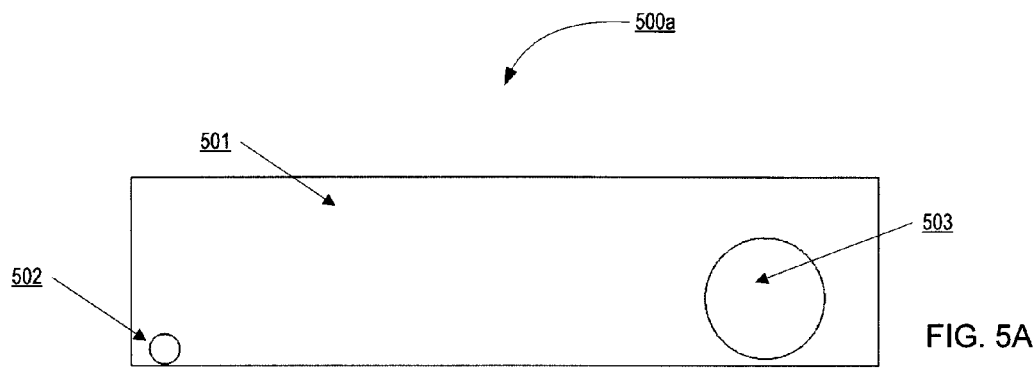
FIG. 5A illustrates a cross-sectional view of an example of a compartment of the structure.
Figure 5B:
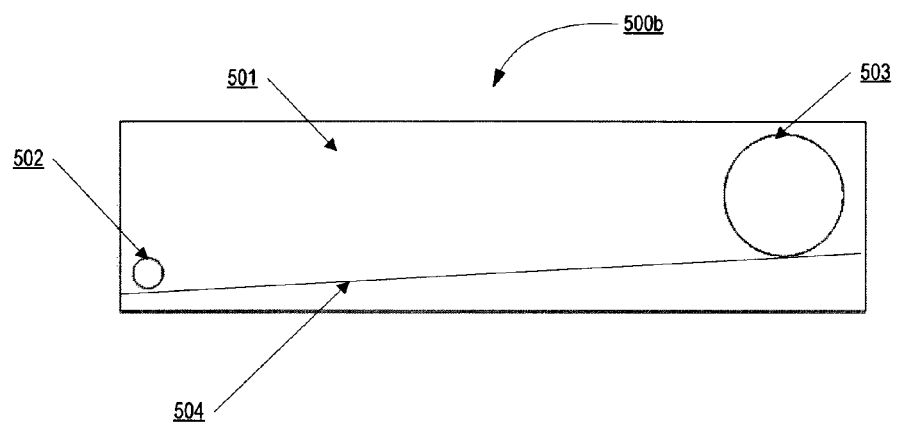
FIG. 5B illustrates a cross-sectional view of another example of a compartment of the structure.
Figure 5C:
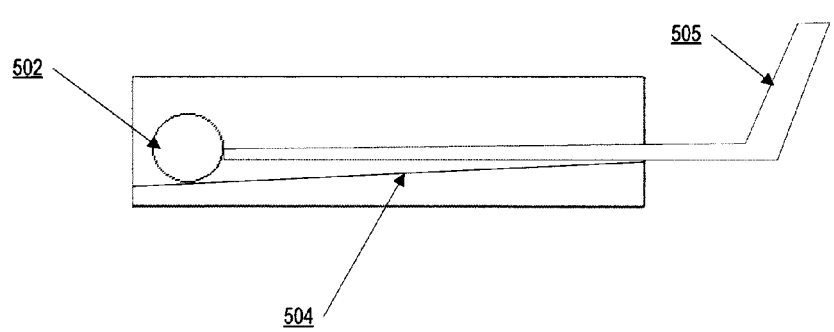
FIG. 5C illustrates an example of access of a cell within a compartment by a microtool.

FIGS. 5A and 5B each show a cross-sectional view of a compartment suitable for a structure in any of the above embodiments. In FIG. 5A, compartment 500a may hold a liquid culture medium 501, a small cell 502 located towards the left (which is the distal end of compartment 501) and a large cell 503 located towards the right (which is the proximal end of compartment 501). In FIG. 5B, compartment 500b may include base 504 downwardly sloped towards the distal end, thereby directing small 502 cell towards the distal end due to gravity. Not immediately apparent from FIG. 5B is that large cell 503 is also directed to roll or migrate towards the distal end by gravity but, due to its size compared to the varying width of the compartment walls, is prevented from rolling or migrating any further towards the distal end. Base 504 may also include one or more sloped surfaces. The sloped surfaces may slope in the direction of movement of a cell due to growth (e.g. from the distal end towards the proximal end), in an opposite direction of cell movement due to growth, or perpendicular to the direction of cell movement due to growth. A number of slopes with the same or different slope orientations may be employed, as required to provide an environment advantageous to the growth of a particular cell. The sloped surfaces may be used to ensure that small, unfertilised oocytes have their approximate midsection exposed if a microtool is held flush against the opening of the compartment. FIG. 5C illustrates how access to small cell 502 may be gained. A microtool 505 may access small cell 502. As illustrated in FIG. 5C, small cell 502 may be pushed by the microtool 505 and be held or pinned close to the distal end. Microtool 505 may access small cell 502 through an access channel adapted for fluid communication between the compartment and the central cavity, initially resting flush against the base of the central cavity so that it is approximately targeted at the centre of a cell due to a slope 504 positioning it lower than the floor or base of the central cavity. In other embodiments (not shown), a microtool may access the small cell by entering through an open top side of the compartment from above.

Figure 6A:
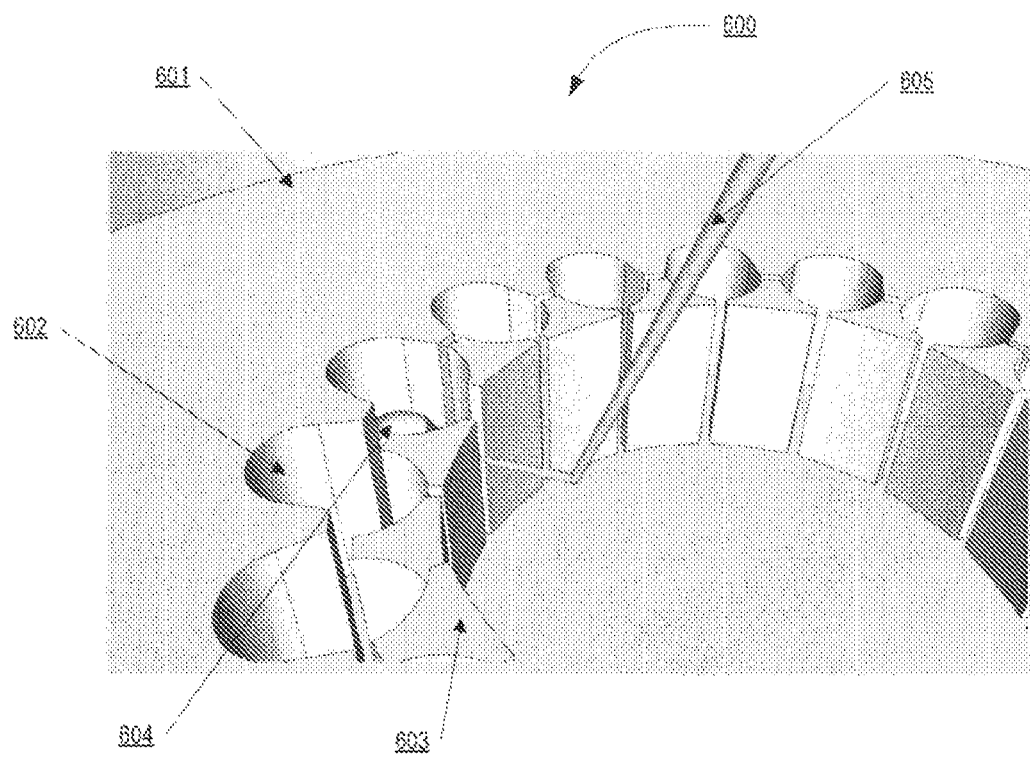
FIGS. 6A and 6B illustrate partial views of a structure with a compartment containing an oocyte.
Figure 6B:
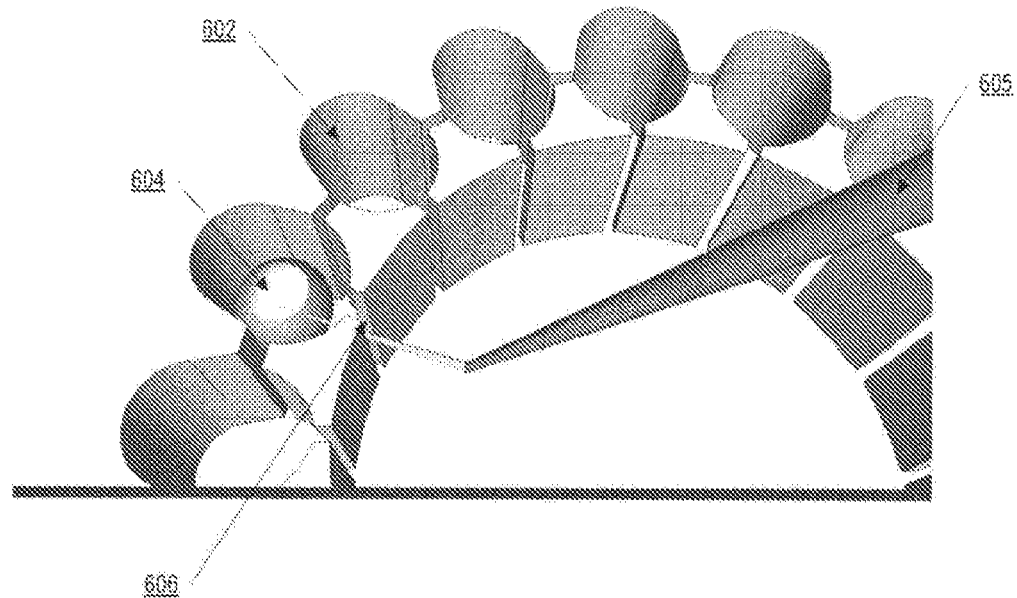

FIGS. 6A and 6B show a partial view of a structure with compartments such as 602 defined between an outer barrier 601 and inner barrier formed by a number of posts such as 603. An oocyte 604 may be accessed by a microtool 605 for implantation or other processes.

Figure 7A:
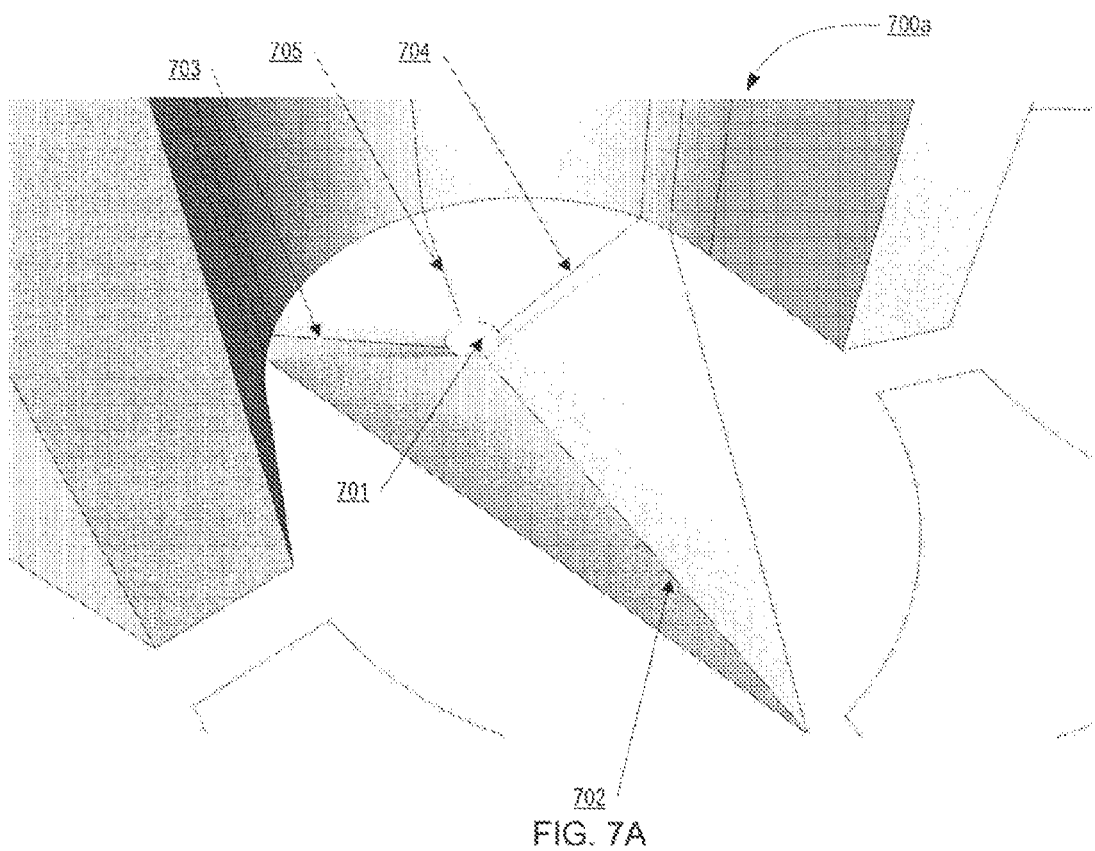
FIG. 7A illustrates a partial view of a structure with a compartment having a base with slope surfaces.

FIG. 7A shows a partial view of a structure with a compartment 700a having a base with sloped surfaces defined by grooves or lines 702, 703, 704 and 705. Compartment 700a may include a primary indentation 701 in which a growing oocyte may rest. The oocyte may be able to expand along groove or line 702 as it grows. Each of grooves or lines 702, 703, 704 and 705 may have a vertical component of approximately the radius r of an oocyte, such that indentation 701 has a depth of approximately r. Posts or inner barrier are not shown for clarity.

Figure 7B:
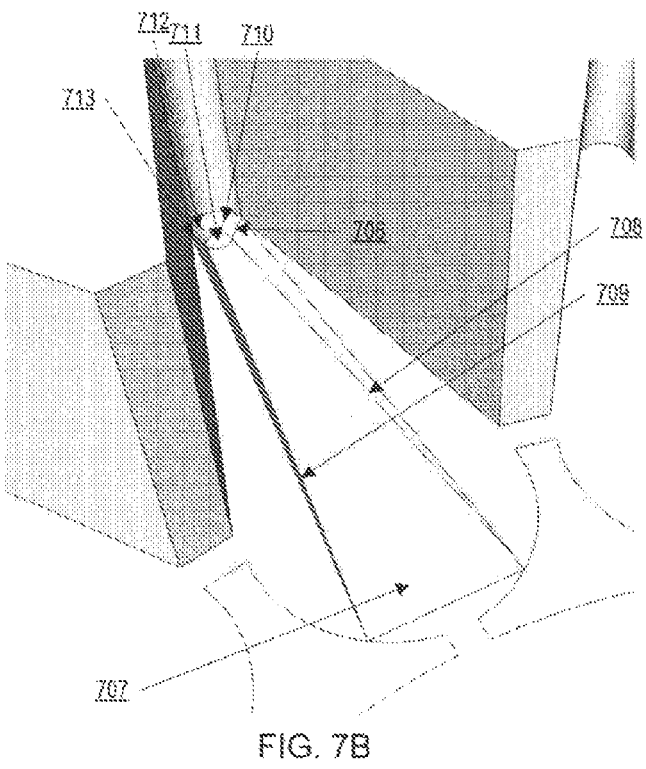
FIG. 7B illustrates a partial view of another structure with a compartment having a base with slope surfaces.

FIG. 7B shows a partial view of another structure with a compartment 700b having a base with sloped surfaces defined by grooves or lines 708, 709, 710, 711, 712 and 713. Compartment 700b may include a primary indentation 706 in which a growing oocyte may rest. As the oocyte grows, it may be able to expand along path 707 which widens towards the proximal end. Each of grooves or lines 708, 709, 710, 711, 712 and 713 may have a vertical component of approximately the radius r of an oocyte, such that indentation 706 has a depth of approximately r. Posts or inner barrier are again not shown for clarity.

In other embodiments, the base of the compartment may additionally or alternatively have curved surfaces. For example, the curved surfaces may curve gradually from one compartment wall to another within the compartment.

Figure 8:
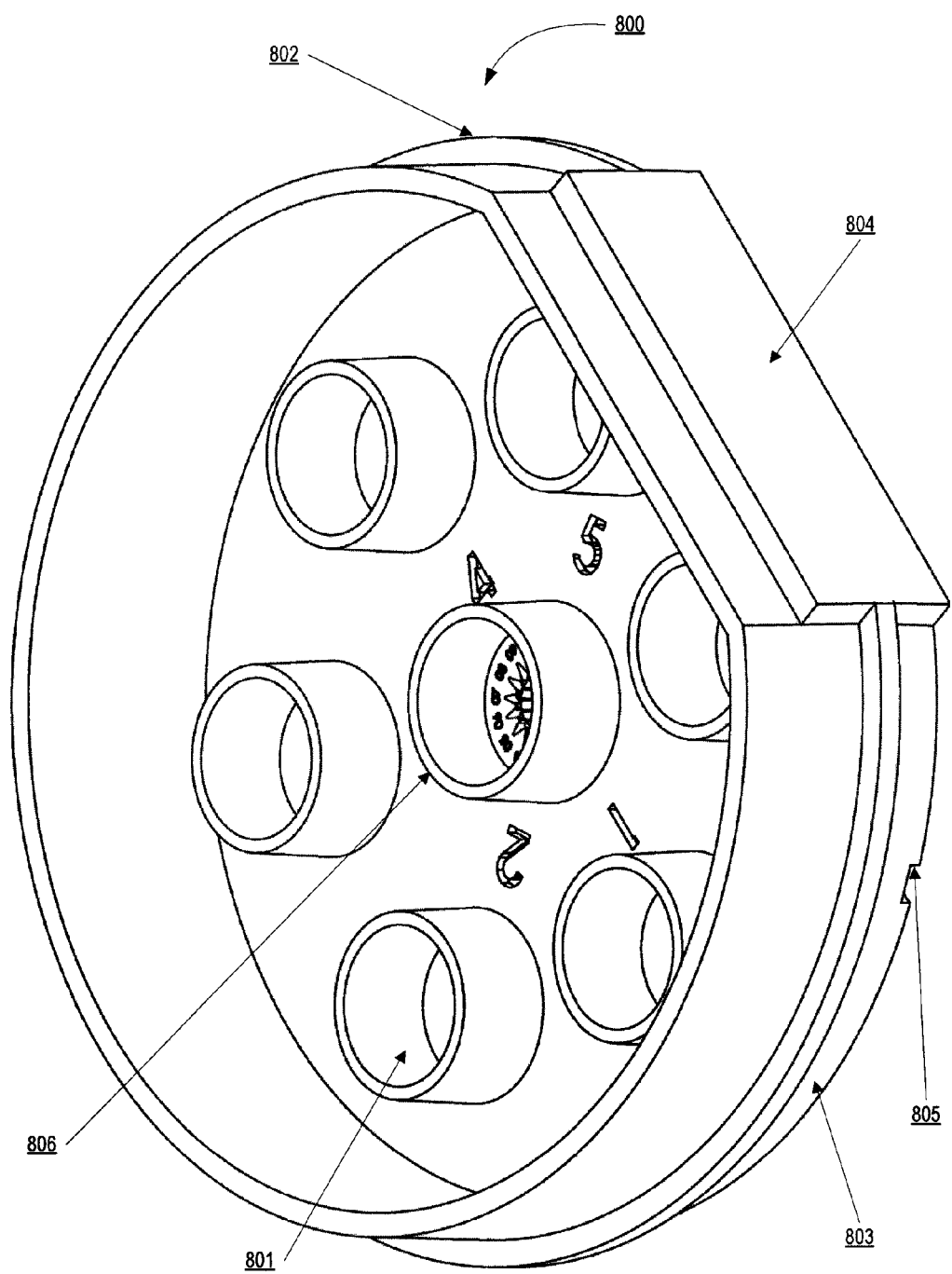
FIGS. 8 and 9 illustrate a perspective view and a top view of another embodiment of a container for culturing cells.

FIG. 8 shows another embodiment of the container 800, which includes a structure 806 located centrally and surrounded by 6 processing wells such as 801. These processing wells take the form of cylindrical wells for intermediate cell culture procedures. The processing wells may be used for gamete pre-processing. For example, the processing wells may be used for sperm processing in an intracytoplasmic sperm injection (ICSI) procedure. In this example, sperm cells are added to one of the processing wells. An appropriate sperm is selected and isolated from the remaining sperms using a viscous medium. The tail of the selected sperm is cut off before the selected sperm is picked up and injected into an egg. In another example, material from an ovary may be processed in a processing well. The intermediate procedures may include identifying viable cells or oocytes for further processing or fertilisation, such as denudation of oocytes to remove extraneous portions of the ovary tissue and cellular matter, such as coronal complexes and cumular cells.

In other embodiments not shown here, there may be more than one structure 806 within a container. At least part of the container may be coated with a coating for one or more of the following: reducing formation of air bubbles caused by flow of the cell culture medium in the container, enhancing adhesion of the cells to a container surface, improving transparency of the container, and improving viability of the cells cultured in the container. The coating may include a hydrophilic or oleophobic substance.

Container 800 includes a rim 802 protruding from the external surface of container 800 to facilitate holding of the dish with a hand or automated gripper. The presence of a rim may reduce the possibility of container 800 slipping or of removing a lid instead of lifting container 800 when a lid is employed.

Container 800 includes a substantially flat surface 804 suitable for writing with a marker or the placement of adhesive labelling, to facilitate identification.

The base 803 of container 800 contains indentations 805 for compatibility with semi-automated or automated conveyor and rotational machinery, facilitating the performance of laboratory procedures on cells inside the features of container 800, and use of automated imaging machinery on, for example, different compartments in the central structure. In one example, container 800 may be placed on a rotatable platform which has radially extending ridges designed to engage corresponding indentations 805. Rotational movements of the platform may therefore rotate container 800 when the radially extending ridges and indentations 805 are properly engaged. An image capturing device such as a camera may be configured to take images at a fixed position offset from the rotational axis of the rotatable platform, so that different compartments of structure 806 (or different processing wells of container 800) may be sequentially imaged as container 800 is rotated by the rotating platform. Similarly, a robotic arm equipped with a microtool may be configured to operate in the vicinity of a fixed position offset from the rotational axis of the rotatable platform, so as to sequentially manipulate cells within different compartments or different processing wells as container 800 is rotated by the rotating platform.

Figure 9:
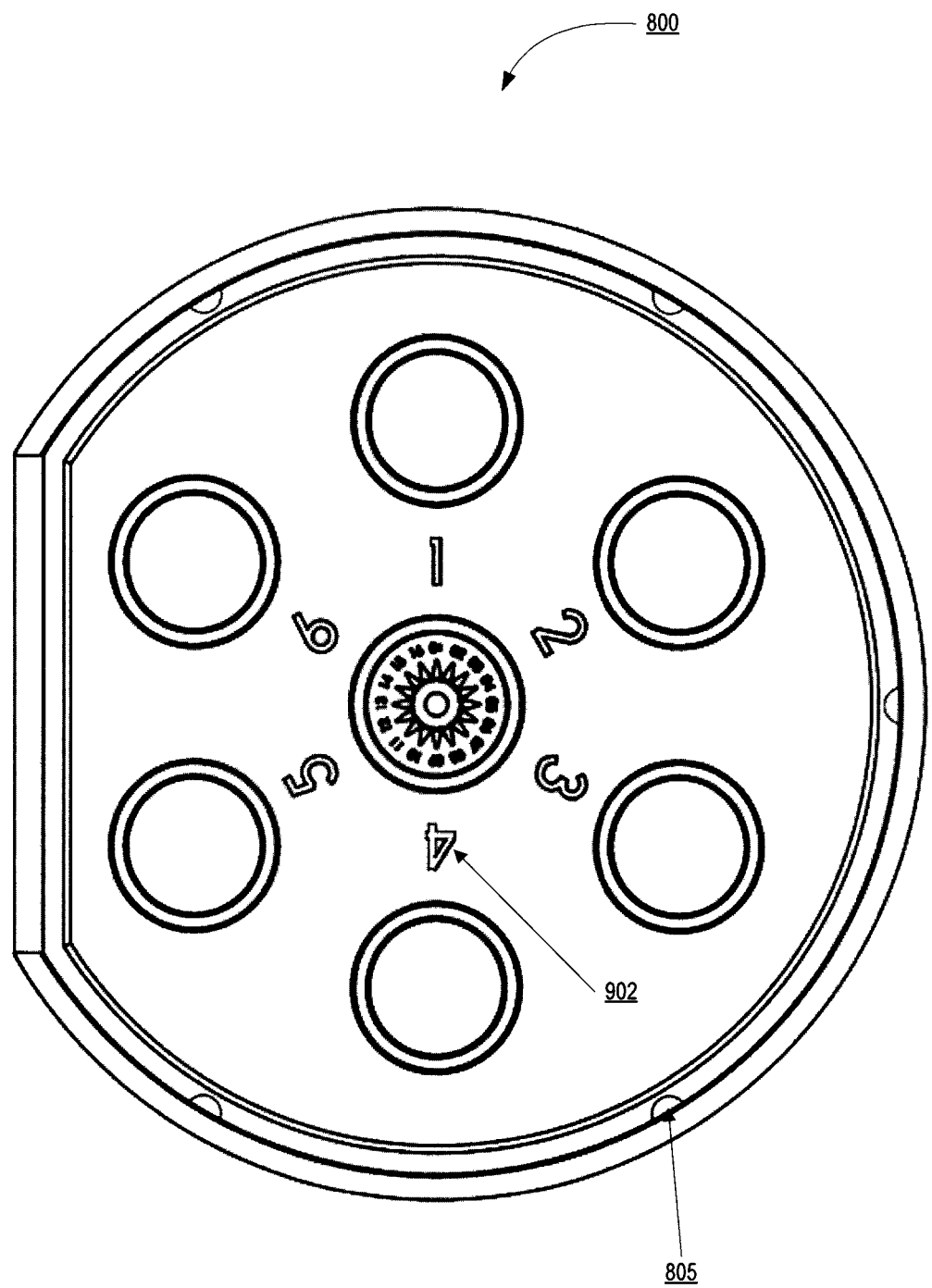

FIG. 9 shows a top see-through view of container 800. Container 800 includes numerical labelling 902 of the processing wells. The labelling may be alphabetical and may be etched into the container, molded as part of the container, or otherwise placed, affixed, or built into container 800. As shown, indentations 805 may be distributed substantially evenly around the perimeter of base 803 of container 800.

Figure 10A:
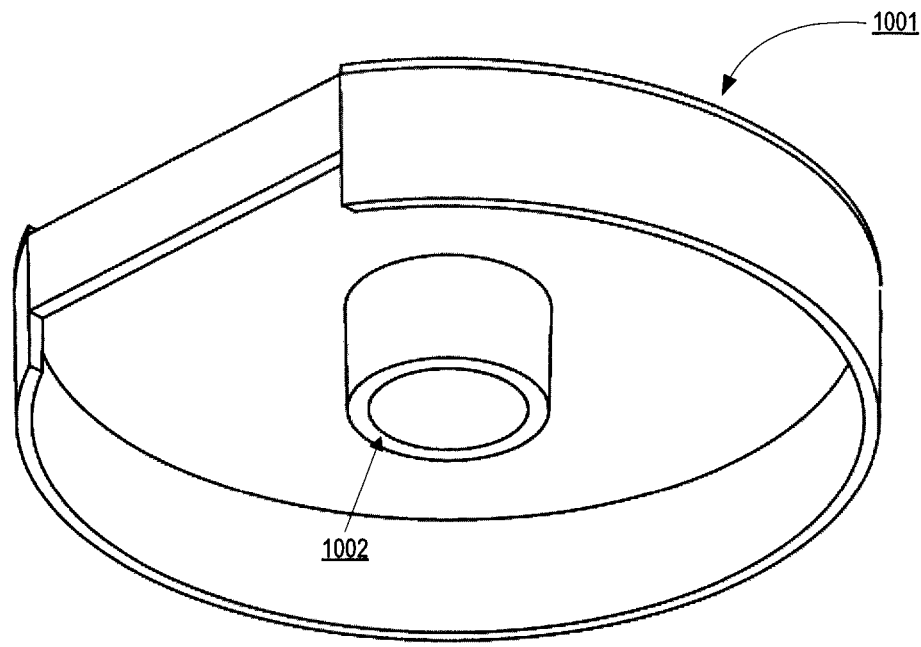
FIG. 10A and 10B illustrate top and bottom perspective views of a lid for the container illustrated in FIGS. 8 and 9.
Figure 10B:
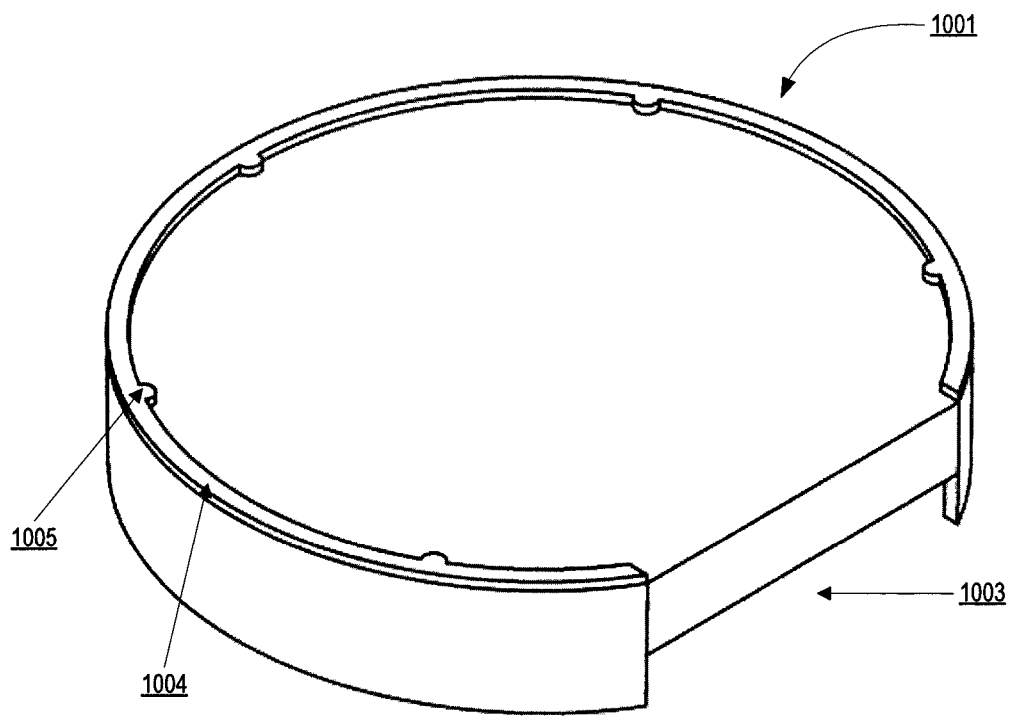
Figure 10C:
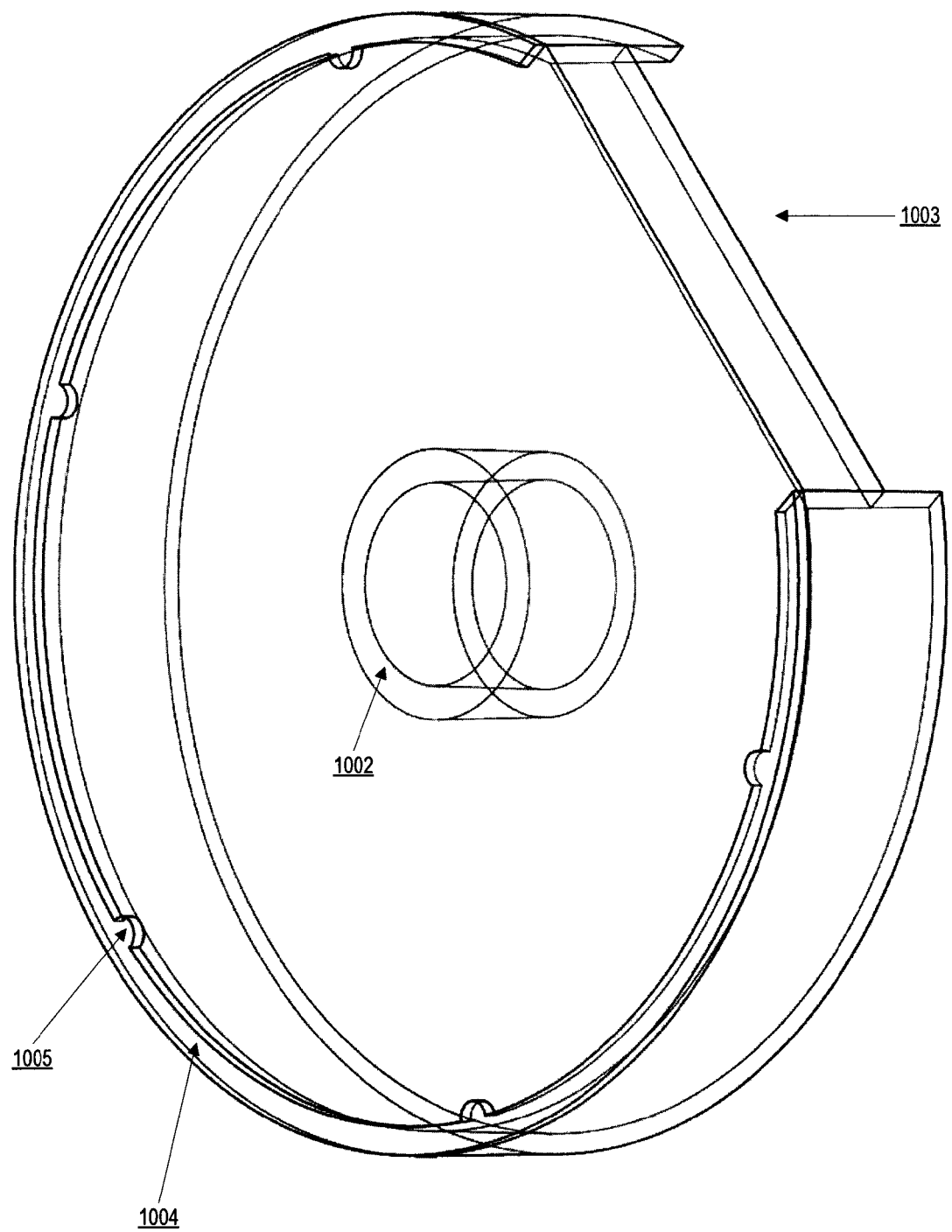
FIG. 10C illustrates a perspective see-through view of the lid illustrated in FIGS. 10A and 10B.

FIG. 10A shows a perspective view of a lid 1001 for use with container 800. The lid 1001 may be transparent and serves to form an airtight, or near-airtight, seal with container 800. The lid 1001 reduces evaporation of liquids or culture medium contained in the central structure 806 of container 800. FIG. 10C shows a see-through version of FIG. 10B.

The lid 1001 includes a tubular extension 1002 which, when container 800 is covered by lid 1001, covers central structure 806 to further reduce evaporation. The lid 1001 may include additional extensions for covering the processing wells in container 800 to reduce evaporation.

The lid 1001 includes a cutout section 1003 which leaves space for a label area such as flat surface 804 shown in FIG. 8.

The lid 1001 may include a raised edge 1004 with protrusions 1005 (corresponding to the indentations 805) which serve to facilitate the stacking of lidded containers and reduce the possibility of lids rotating, moving, or slipping when the containers are stacked.

Figure 11A:
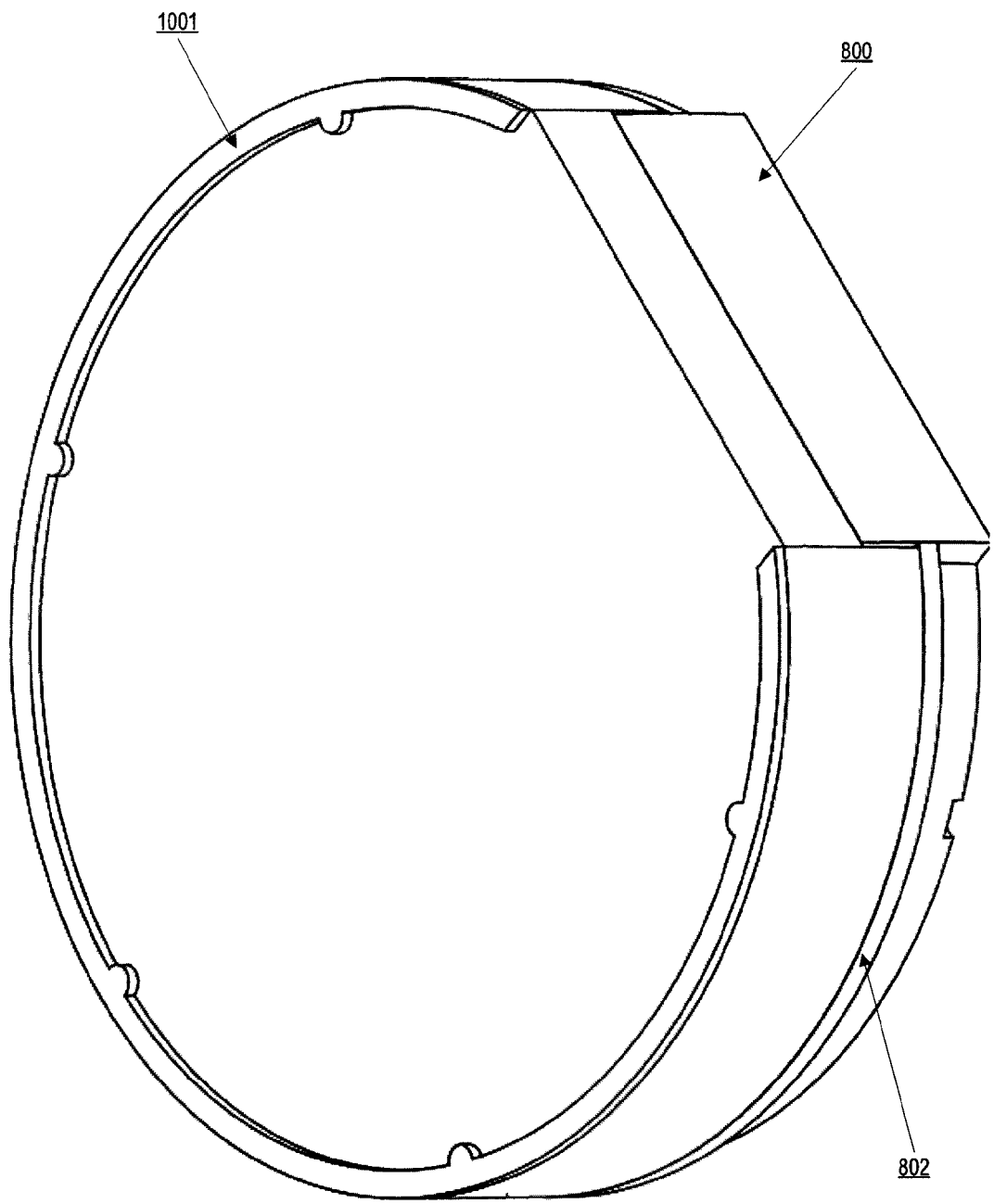
FIG. 11A illustrates a perspective view of the container illustrated in FIGS. 8 and 9 covered with the lid illustrated in FIG. 10.
Figure 11B:
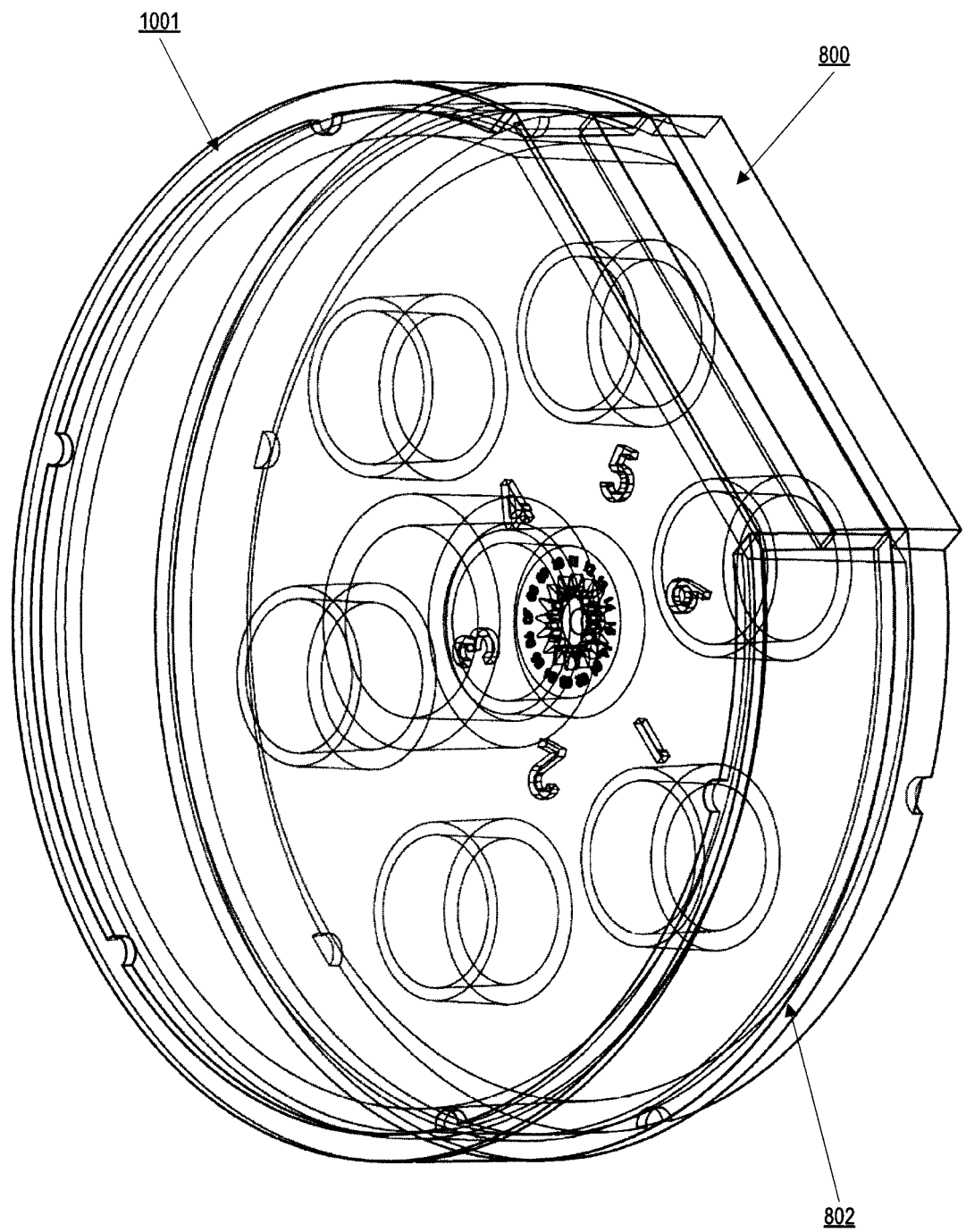
FIG. 11B illustrates a perspective see-through view of the lidded container illustrated in FIG. 11A.

FIG. 11A shows container 800 covered with lid 1001. FIG. 11B shows a see-through version of FIG. 10A. The rim 802 may serve as an abutment between the lid 1001 and container 800, or lid 1001 may fit snug with the top of container 800.

Figure 12:
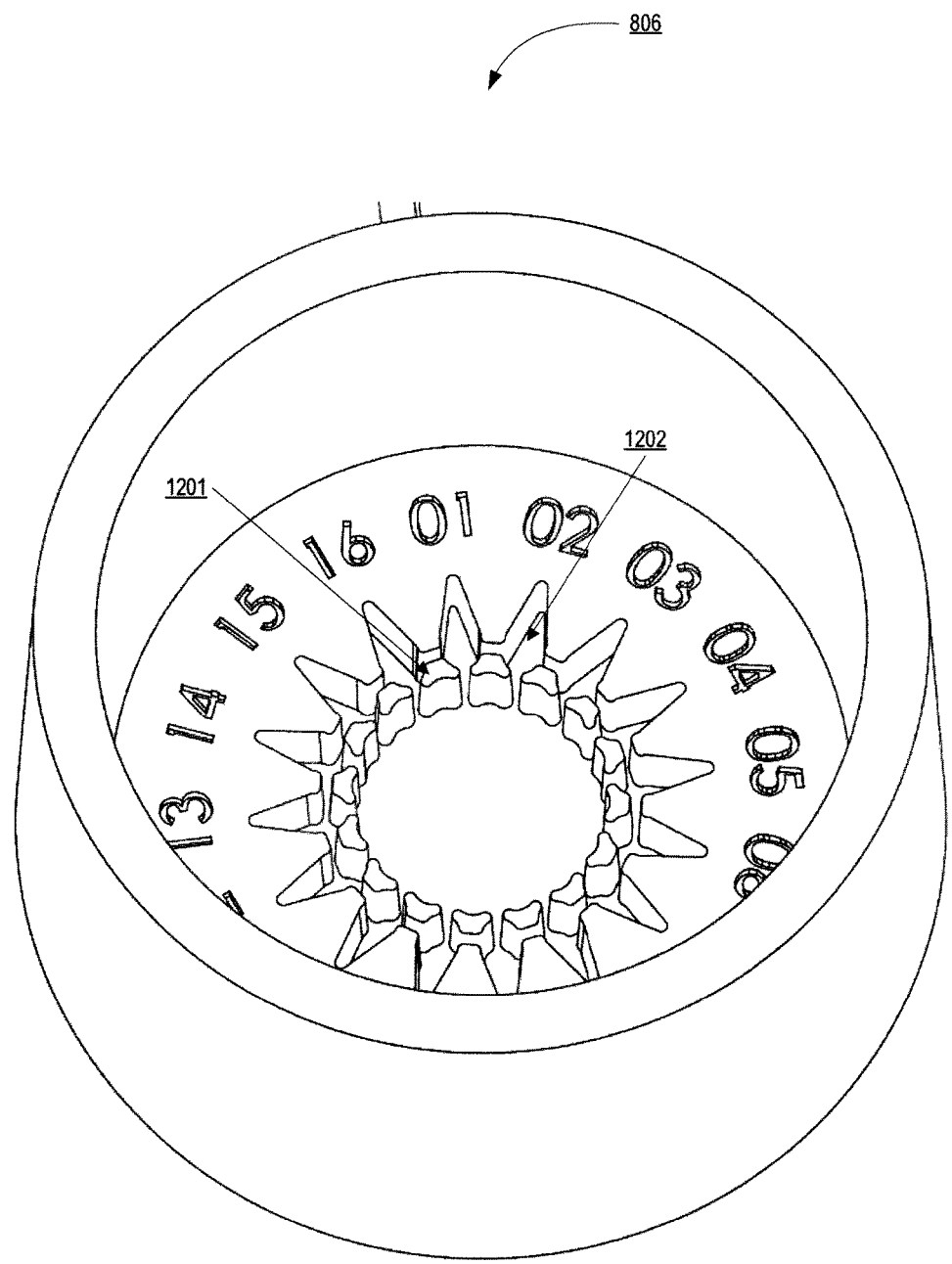
FIG. 12 illustrates a perspective view of an embodiment of a structure illustrated in the container of FIGS. 8 and 9.

FIG. 12 shows a close-up of central structure 806. Structure 806 includes an inner barrier formed by rounded polygonal posts 1201. An outer barrier defines separate compartments (such as 1202) in direct fluid communication with each other.

Now that embodiments of the structure and the container have been described, it should be apparent to a skilled person in the art that the described arrangements include the following advantages:

- The shape of the compartment offers a limited area or space that a cultured cell is able to occupy, with its location within the compartment determined by its size, which in some cases may be in turn determined by its age or stage of maturation. This enables visual identification and monitoring of the state of the cultured cell, and facilitates access to the cultured cell by a microtool since the shape of the compartment assists to hold the cell in place for manipulation.
- The described arrangements enable multiple cultured cells, which may be human or animal zygotes, to be held in close proximity. This may improve the viability of certain cell cultures.
- The shape of the compartment also makes it easy to hold a small cell in place at the distal end of the compartment when attempting to manipulate the cell with a microtool. For example, a small oocyte could very easily be fertilised in this way as the compartment naturally holds the oocyte in place when it is pushed to the narrower distal end with the microtool.
- The small dimensions of the compartment enable the use of very small volumes of cell culture medium, reducing costs associated with cell culture and/or enabling the use of superior, more expensive culture media.

The compartment base may include sloped surfaces, encouraging cells of varying states of maturation to occupy certain areas within the compartments. This may be advantageous in ensuring the approximate centre of an oocyte is in line with the floor of the central cavity, thereby simplifying microtool operations.

The additional processing wells enable a single culture dish to be employed for the entire cell culture process, reducing consumable costs and laboratory time required to perform a cell culture procedure.

The large number of wells enables fewer culture dishes to be employed for a single culture procedure—for example, most human patients would only require a single dish. This reduces consumable costs and laboratory equipment costs, taking up less space in cell culture incubators.

The one or more supports on the outer bottom surface of the container allow airflow under the dish, preventing condensation from causing optical defects when cells are viewed under a microscope.

The one or more indentations on the base allow ease of rotation or manipulation by semi-automated or automated machinery, improving the efficiency of cell manipulation processes in the laboratory or clinic.

The lid prevents accidental contamination while facilitating identification for reducing potential laboratory error.

Those skilled in the art will appreciate that the invention described herein is susceptible to variations and modifications other than those specifically described. For example, in some embodiments, each of the plurality of compartments may be configured to hold a single cell. In some other embodiments, each of the plurality of compartments may be configured to hold more than one cell. A cell may be any type of cell, including but not limited to one or more of a sperm cell, an egg cell and an oocyte. The cross-section of the posts defining the inner barrier may be of a square, pentagon, hexagon or any other shape. All such variations and modifications are to be considered within the ambit of the present invention the nature of which is to be determined from the foregoing description.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A structure for use with a container for culturing multiple cells, the structure comprising:
   a partially enclosed cavity; and
   a plurality of compartments each having a proximal end adjacent to the partially enclosed cavity, a distal end remote from the partially enclosed cavity and a space between the proximal end and the distal end, wherein:
   each compartment is provided with an access channel for fluid communication with the partially enclosed cavity, each compartment is configured to hold a cell at a location in the space between the proximal end and the distal end, and each compartment is shaped to increase in width towards the proximal end to facilitate movement of the cell upon growth towards the proximal end, and
   at least one of the plurality of compartments is provided with an inter-compartment channel for direct fluid communication with an adjacent one of the plurality of compartments.

2. A structure of claim 1 wherein the plurality of compartments each include a sloped base for positioning the cell within the respective compartment.

3. A structure of claim 2 wherein the sloped base is downwardly sloped towards the distal end.

4. A structure of claim 2 wherein the sloped base includes one or more grooves.

5. A structure of claim 1 further including the one or more access channels or the one or more openings for facilitating access by a microtool.

6. A structure of claim 1 further comprising:
   an inner barrier for defining the partially enclosed cavity; and
   an outer barrier for defining the plurality of compartments between the inner barrier and the outer barrier.

7. A structure of claim 6 wherein the inner barrier includes posts.

8. A structure of claim 7 wherein the posts include one or more of circular posts, triangular posts and polygonal posts.

9. A structure of claim 7 wherein the posts define the one or more access channels or the one or more openings.

10. A structure of claim 6 further comprising a wall coupled to the outer barrier for containing a culture medium.

11. A structure of claim 1 wherein the cavity includes a central cavity surrounded by the plurality of compartments.

12. A structure of claim 11 wherein the plurality of compartments are equidistant or substantially equidistant from the central cavity.

13. A structure of claim 1 wherein at least one of the plurality of compartments is labelled.

14. A structure of claim 13 wherein the labelling includes any one or more of etching, engraving, embossing and molding.

15. A structure of claim 1 wherein at least one of the plurality of compartments is configured to hold more than one cell.

16. A structure of claim 1 wherein the cell includes any one or more of a sperm cell, an egg cell, an oocyte, a zygote and a blastoma.

17. A container for culturing multiple cells, including or formed integrally with a structure, the structure comprising:
   a partially enclosed cavity; and
   a plurality of compartments each having a proximal end adjacent to the partially enclosed cavity, a distal end remote from the partially enclosed cavity and a space between the proximal end and the distal end, wherein:
   each compartment is provided with an access channel for fluid communication with the partially enclosed cavity, each compartment is configured to hold a cell at a location in the space between the proximal end and the distal end, and each compartment is shaped to increase in width towards the proximal end to facilitate movement of the cell upon growth towards the proximal end, and
   at least one of the plurality of compartments is provided with an inter-compartment channel for direct fluid communication with an adjacent one of the plurality of compartments.

18. A container of claim 17 further including one or more supports for elevating the container to permit airflow underneath the container.

19. A container of claim 17 wherein the container is a sample dish.

20. A container of claim 19 wherein the sample dish is a Petri dish.

21. A container of claim 17 further including one or more indentations arranged around a base to facilitate orientation or rotation.

22. A container of claim 21 further including one or more protrusions corresponding to the one or more indentations, the protrusions arranged around a lid to facilitate orientation or stacking.

23. A container of claim 17 wherein at least part of the container is coated with a coating for any one or more of the following:
   reducing formation of air bubbles caused by flow of the cell culture medium in the container;
   enhancing adhesion of the cells to a container surface;
   improving transparency of the container; and
   improving viability of the cells cultured in the container.

24. A container of claim 23 wherein the coating includes a hydrophilic or oleophobic substance.

\* \* \* \* \*